US007052723B1

(12) United States Patent
Tierra

(10) Patent No.: US 7,052,723 B1
(45) Date of Patent: May 30, 2006

(54) METHOD AND COMPOSITION FOR TREATMENT OF AQUATIC ANIMALS

(75) Inventor: Michael Robert Tierra, Ben Lomond, CA (US)

(73) Assignee: NOvalek, Inc., Hayward, CA (US)

( * ) Notice: Subject to any disclaimer, the term of this patent is extended or adjusted under 35 U.S.C. 154(b) by 201 days.

(21) Appl. No.: 10/212,285

(22) Filed: Aug. 1, 2002

(51) Int. Cl.
*A61K 35/78* (2006.01)
*A01K 69/00* (2006.01)

(52) U.S. Cl. ........................ 424/771; 119/115; 119/231

(58) Field of Classification Search .................. 424/771
See application file for complete search history.

(56) References Cited

U.S. PATENT DOCUMENTS 3,602,194 A * 8/1971 Marking ..................... 119/231
6,164,244 A * 12/2000 Cutler et al. ................ 119/215
6,340,468 B1 * 1/2002 Cutler et al. ................ 424/405

* cited by examiner

*Primary Examiner*—Herbert J. Lilling

(74) *Attorney, Agent, or Firm*—Harris Zimmerman

(57) ABSTRACT

A composition and method is disclosed for suppressing infections and treating one or more injured or diseased aquatic vertebrate animals, by adding to the water containing the aquatic animal(s) a solution containing the extracted juice and fine particles of walnut husks or the combination of walnut husks and walnut leaves of the walnut trees of the genus *Juglans*, family Juglandaceae (also referred to herein as "*Juglans* blend"). Effective amounts of walnut husks or the combination of walnut husks and walnut leaves which inhibit or promote recovery from aquatic bacterial, fungal, protozoan, and dinoflagellate diseases on the surface of or in the skin of the animal or from wounds and abrasions, or to control or eliminate metazoan parasites, or to control or eliminate aquatic single-celled green algae are in the range from 0.035 grams to 0.085 grams of dried walnut husks or walnut husks and walnut leaves prepared as a blend, and added as a standard daily dose per 10 gallons of water until the treatment is completed, which is within several days to several weeks. These walnut husks and leaves come from species of the genus *Juglans* (species *nigra, cinerea*, and *regia*) that are presently grown across the United States and in other temperate regions of the world.

4 Claims, No Drawings

METHOD AND COMPOSITION FOR TREATMENT OF AQUATIC ANIMALS

FIELD OF THE INVENTION

The present invention concerns the use of a mixture of nut husks of walnut trees or a mixture of walnut husks and walnut leaves as a therapeutic and prophylactic treatment of aquatic vertebrate animals—more particularly, for the treatment of fishes, amphibians, and aquatic reptiles, and the reduction and elimination of single-celled aquatic algae, generally called aquatic green algae.

BACKGROUND OF THE INVENTION

Diseases and injuries are not only detrimental to the physiological well being of live fishes and other aquatic vertebrate animals, but also can adversely affect the physical appearance of otherwise viable animals. The prevention, control and treatment of diseases and injuries is particularly important for fishes and other aquatic vertebrate animals that are kept in artificial or confined environments such as in aquariums, bowls, tanks, troughs, or in ponds, such as in pet aquarium keeping, public aquariums, ornamental ponds, or in aquiculture ponds and other aquiculture enclosures, as well as in shipping containers for aquatic animals such as in water tanks and in barrier and breathing plastic bags. Tens of millions of live aquatic vertebrate animals are transported annually around the world carrying the disease organisms and parasites of their origin, as well as sold in the United States to buyers keeping them alive. Adequate treatments are vitally needed to reduce and eliminate such diseases and parasites, particularly so by a means that is harmless to vertebrates, including man and his pet animals.

SUMMARY OF THE INVENTION

This invention is a therapeutic and prophylactic composition and method for treating fishes, amphibians, and aquatic reptiles, by administering into the water environment in which they are living the mixture or blend prepared from walnut husks or from the combination of walnut husks and walnut leaves. The mixture is to be an amount effective to promote recovery of such diseased or parasitized aquatic vertebrate animals or to prevent diseases, parasites, and pestiferous organisms from occurring or surviving.

This invention which comprises an aqueous mixture or blend containing the juice and fiber from walnut husks or from the combination of walnut husks and walnut leaves is a composition which also serves as a suppressant and/or eliminator of aquatic green algae.

Chemicals such as malachite green, formalin, trichlorfon and others have been used for decades in treating external infections and parasites in aquatic vertebrate animals but they are of danger to man and are variously regulated in the United States by the EPA (Environmental Protection Agency) and FDA (Food and Drug Administration) in such uses. Antibiotics that have been developed for human treatments have also been used with aquatic animals against bacteria, but have been variously regulated by the FDA for aquatic animals, so as to conform with their regulation of these drugs for human use.

The present invention involving the use of walnut husks and leaves is effective for treating living aquatic vertebrates of all types and species, afflicted with, or subjected to, or susceptible to aquatic bacterial diseases, fungal diseases, and protozoan and dinoflagellate diseases, or injuries such as wounds, abrasions, and the like. Also, the invention regarding the use of walnut husks and leaves is effective in inhibiting the growth of or eliminating aquatic metazoan parasites and aquatic single-celled green algae. Walnut husks or walnut husks and walnut leaves ("*Juglans* blend") are to be administered by introducing an aqueous blend comprising walnut husks or walnut husks and walnut leaves into the water containing the aquatic animals to be treated. The blend of these ingredients does not adversely affect healthy aquatic vertebrates. Healthy vertebrates can remain in the water in which the infected animals are being treated with the "*Juglans* blend". Humans can handle the blend of walnut husks and leaves without the blend being regarded as a harmful substance. The blend is also harmless to pet animals such as dogs and cats.

DESCRIPTION OF THE PREFERRED EMBODIMENTS OF THE INVENTION

The primary active ingredients for the aquatic animal treatment method are walnut husks or a mixture of walnut husks and walnut leaves. As used herein, "walnut husks or walnut husks and walnut leaves" are the substances obtainable from walnut trees of the genus *Juglans*, including the species *nigra* (black walnut). *cinerea* (butternut or white walnut), and *regia* (English walnut). These trees are presently grown world wide in temperate climates. References to walnut husks and walnut leaves in this disclosure include the liquids and fibrous constituents obtained from them. The walnut parts utilized in this invention is a mixture of components found in the walnut husks and in the walnut leaves, rather than a single component fractionally distilled and separated from them. It has been known for centuries that ingredients in the husks of the nuts of walnut trees exert anti-fungal, anti-helminthic, anti-bacterial, anti-protozoal and anti-tumor effects. A primary active constituent in walnut trees has been identified as a naphthoquinone, which is mainly found in nut hulls of walnut trees, most potently in black walnut (*Juglans nigra*). The most effective test results in the treatments were obtained from the use of black walnut (*Juglans nigra*) nut husks.

The composition of walnut husks or the combination of walnut husks and walnut leaves may be used with other ingredients enhancing its efficacy, including garlic (*Allium sativum*), mugwort (*Artemisia vulgaris*), and clove oil (*Syzygium aromaticum*). Walnut husks and walnut leaves can be used as a mixture in a liquid, or adsorbed onto or absorbed into a solid carrier or substrate, such as tablets, or associated with other vehicles, provided that such are compatible with the administration of the walnut husks and walnut leaves into water containing the aquatic animal(s) to be treated, and do not adversely affect the aquatic animal(s) being treated or other beneficial aquatic life in the water.

The procedure for production of the "*Juglans* blend" is as follows. To each 25 gallons of de-ionized water add 18 lbs. Of walnut tree whole nut husks (or 14 lbs of husks and 4 lbs of whole walnut tree leaves) which have been fragmented in a hammer mill and are wrapped in cotton cloth or muslin, and are added to a stainless steel container in which the water is boiling hot. The heat is turned down to a simmering level. After simmering for 40 minutes the mixture is removed from the heat source. When other herbs are to be added, Mugwort (*Artemisa vulgaris*, 32 ounces per original 25 gallons) and Garlic (*Allium sativum*, 96 ounces per original 25 gallons) in dried form are wrapped in cotton cloth or muslin and are added at this time (40 minutes after the walnut ingredients are added). After the mixture has cooled two hours, then the cotton cloth or muslin wrappings with the remainder of the husks (and leaves) and Mugwort and Garlic are removed. When clove oil (*Syzygium aromaticum*, 1 ounce per original 25 gallons) is added to the mixture, it is done at this time. In all formulations the final ingredient is now added to the mixture, Potassium Sorbate in the ratio of 8 oz potassium sorbate per 25 gallons of the original amount of de-ionized water. After mixing, the resulting liquid blend is trained and bottled, termed herein as the "*Juglans* blend". Macerating 4 ounces of dried walnut husk powder in a solution containing the same amount of de-ionized water and ethanol alcohol will also produce a form of the "*Juglans* blend."

A standard minimum treatment is based on using 1 teaspoon (⅙ fluid ounce,=5 ml) of the "*Juglans* blend" in 10 gallons (37.85 liters) of water containing the aquatic animal(s) to be treated, or fraction thereof, if treatment is in less water. The standard treatment can vary from being daily to twice a day, as well as being based on using more than 1 teaspoon (⅙ fluid ounce,=5 ml) per dose, such as in a double dose. The "*Juglans* blend" can be used equally effectively in fresh water, brackish water, or salt water—in aquariums, ponds, as well as in shipping containers, such as tanks and plastic bags used for transporting fishes.

The walnut husks and leaves comprise about 3.75% to 8.84% of the liquid volume in the "*Juglans* blend".

A standard dose of the "*Juglans* blend" contains from 0.035 to 0.085 grams of dried weight of walnut husks or of walnut husks and walnut leaves.

DESCRIPTION OF TEST PROCEDURES AND RESULTS OF THE INVENTION

The following fresh water, brackish water, and salt water fish species, and fresh water amphibian and aquatic reptile (turtle) species have been variously treated successfully with a range of amounts of the "*Juglans* blend" with the primary ingredients being walnut tree nut husks and leaves of the black walnut (*Juglans niger*) to eradicate infections completely, and as a prophylactic to inhibit infections occurring. The most effective ingredient was determined to be the nut husks, and an effective amount and procedure for preparation is as described above. The procedures followed in the production of the "*Juglans* blend" for the treatments are as described for this invention. Each test lasted several days to three weeks in duration for eradication of external infections on the surface of the test animals of bacteria, protozoans, dinoflagellates, fungus, as well as in reduction in number and in some cases eradication of external infections of crustaceans (fish lice) and worms (trematodes), and in the reduction or eradication of aquatic single-celled green algae (Chlorophyeae). The family name and species names of the test animals listed below are the scientific names recognized in ichthyology and herpetology.

Over 100 individual aquaria with individual filter systems 15–45 gallons in size were used in the tests, testing a total of 1716 freshwater, 314 brackish and saltwater fishes, 144 reptiles—65 amphibians, and 79 aquatic turtles. Thousands of aquarium and ornamental pond fishes of approximately 30 families) were tested in multiple aquaria with integrated test aquarium systems that are not enumerated here (see Test Examples 4 and 5 below), with fishes up to 20" in length, amphibians up to 5" in length, and reptiles (turtles) up to 4" in length. It is postulated that sufficient numbers and kinds of fishes were tested to consider that in general the treatment with "*Juglans* blend" as presented herein will be a successful treatment for most or all kinds of fishes, amphibians and aquatic turtles kept in aquariums and ponds.

Those disease organisms which are common external infections of fishes were identified as:

(1) Bacteria: Furunculus=ulcer disease *Aeromonas hydrophila* and *Pseudomonas flourescens, Bacillus, Vibrio, Salmonella.*

(2) Fungus: *Saprolegnia Icthyophorus hoferi, Exophiala* sp., Sea horse disease, *Exophiala*

(3) Protozoans: "Ich" *Ichthyophthirius multifilis, Chilodonella ciprinii*, "Guppy Killer" *Tetrahymena pyriformis*, "Hole in the Head Disease" *Hexamita* sp., "Costia" *Ichthyobodo necatrix, "Trichodoniasis" Trichodina* or *Trichodonella*, "Myxosporidiosis" Henneguya (4) Dinoflagellates: Oodinium, Amyloodinium, Crepidoodinium, The numbers for the categories of disease organisms are listed in the "Infection" column when there is more than one infection for that category. The total number of specimens treated of each species of fish, amphibian and reptile are listed under "Number Treated". This list only includes those animals that were treated in individual aquariums, each with its own separate filtration. Treatments for fishes (Test Examples 4 and 5), and amphibians under other conditions (Test Example 4 and 6) are described under "Test Examples" below.

(5) Metazoan Parasites: Crustacean Fish Lice Argulus, Ergasilis, Anchor Worms Lernaea, In addition, observations were made on the effect of the "*Juglans* blend" on green algae in the water: Chlorella, Chlorophyceae.

Freshwater Fishes

| FAMILY | COMMON NAME | SPECIES NAME | INFECTION | NUMBER TREATED |
|---|---|---|---|---|
| Ambassidae | Glass Fish | *Ambassis lala* | Fungus, Ich | 22 |
| Characidae | Black Tetra | *Gymnocorymbusa ternetzi* | Fungus, Ich | 23 |
| | Neon Tetra | *Hyphessobrycon innesi* | Ich | 38 |
| | Cardinal Tetra | *Cheirodon axelrodi* | Ich, Fungus, (1) | 71 |
| | Glow Light Tetra | *Hemigrammus erythrozonus* | Ich | 8 |
| | Rummy Nose Tetra | *Hemigrammus rhodostomus* | Ich, Fungus | 25 |
| | Black Tetra | *Gymnocorimbus ternetzi* | Ich | 36 |
| | Flame Tetra | *Hyphessobrycon flammeus* | Ich | 5 |
| | Rosy Tetra | *Hyphessobrycon rosaceus* | Ich | 12 |
| | Red Hooked Dollar | *Serrasalmus striolatus* | Ich, Fungus | 28 |
| | Silver Dollar | *Metynnis argenteus* | Ich | 36 |
| Cichlidae | Jewelled Cichlid | *Hemichromis bimaculatus* | Fungus (1) | 8 |
| | Discus | *Symphysodon discus* | (2) | 14 |
| | Ram | *Apistogramma ramiresi* | Ich | 24 |
| | Jurupari | *Geophagus jurupari* | Ich, Fungus | 6 |
| | Firemouth | *Cichlasoma meeki* | Ich, (1), Fungus | 9 |
| | Jack Dempsey | *Cichlasoma biocellatum* | Ich, Fungus | 13 |
| | Oscar | *Astronotus ocellatus* | Hexamita, Ich, (4) | 22 |

-continued

Freshwater Fishes

| FAMILY | COMMON NAME | SPECIES NAME | INFECTION | NUMBER TREATED |
|---|---|---|---|---|
| | Angel Fish | *Pterophyllum scalare* | Ich, Fungus | 108 |
| | | *Tropheus duboisi* | Ich | 4 |
| | Mozambique Tilapia | *Tilapia mossambica* | Ich, (5) | 6 |
| | Flag Acara | *Cichlasoma festivum* | Ich, Fungus | 21 |
| | Red Devil | *Lamprologus* sp hybrid | Ich, Fungus, (1) | 38 |
| | | *Haplochromis obliquidens* | Ich | 5 |
| | Banded Cichlid | *Cichlosoma severum* | Ich | 12 |
| | | *Geophagus* sp. | Ich, Fungus | 7 |
| Poecilii-dae | Black Molly | *Mollienisia sphenops* | Ich | 24 |
| | Red Sword-tail | *Xiphophorus helleri* | Ich, Fungus | 42 |
| | Platies | *Xiphophorus maculatus* | Ich, Fungus | 120 |
| | Guppies | *Lebistes reticulatus* | (3) Fungus | 280 |
| | Black Sailfin Molly | *Poecilia velifera* | (3) Fungus | 48 |
| Cy-prinidae | Comet Gold-fish | *Carassius auratus* | Trichodon-ella, Ich, (5) | 25 |
| | Black Moor Goldfish | *Carassius auratus* | Ich, Fungus | 5 |
| | Bubble-eye Goldfish | *Carassius auratus* | Ich, Bacteria | 7 |
| | Giant Danio | *Danio aequipinnatus* | Ich | 29 |
| | Pearl Danio | *Brachydanio albolineatus* | Protozoans | 37 |
| | Zebra Fish | *Brachydanio rerio* | Ich | 27 |
| | White Cloud | *Tanichthys albonuhes* | Ich, (1) | 18 |
| | Rasbora | *Rasbora heteromorpha* | Ich | 7 |
| | Rosy Barb | *Puntius conchonius* | Bacteria, Ich | 19 |
| | Cherry Barb | *Puntius titteya* | Ich | 15 |
| | Stoliczka's Barb | *Puntius stoliczkanus* | Ich | 12 |
| | Koi | *Cyprinus carpio/ Carassius auratus* | Ich, Fungus, (1) (5) | 280 |
| | Red-tailed Shark | *Labeo bicolor* | Ich, Fungus | 21 |
| | Bala Shark | *Balantocheilos melanopterus* | Ich, Fungus | 18 |
| | Stolizka's Barb | *Puntius* sp. | Protowans | 8 |
| Anabanti-dae | Blue Gourami | *Trichogaster trichopterus* | Ich | 28 |
| | Pearl Gourami | *Trichogaster leeri* | Ich | 31 |
| | Kissing Gourami | *Helostoma temmincki* | Ich | 5 |
| | Honey Gourami | *Colisia fasciata* | Ich, Fungus | 12 |
| | Dwarf Gourami | *Colisa lalia* | Ich, (1) | 15 |
| | Fighting Fish | *Betta splendens* | Protozoans | 37 |
| Melan-otaeniidae | Rainbow Fish | *Mclanotaenia affinis* | Ich | 3 |
| Cobitidae | Clown Loach | *Botia macracantha* | Ich | 7 |
| Doradidae | Striped Spiny Catfish | *Platydoras costatus* | Ich, Fungus | 3 |

-continued

Freshwater Fishes

| FAMILY | COMMON NAME | SPECIES NAME | INFECTION | NUMBER TREATED |
|---|---|---|---|---|
| Callich-thyidae | Bronze Cat-fish | *Corydoras aeneus* | Henneguya, Ich | 39 |
| | Bowline Catfish | *Corydoras arcuatus* | Ich | 12 |
| | Peppered Catfish | *Corydoras paleatus* | Ich | 13 |
| | Micro Cat-fish | *Corydoras hastatus* | Ich | 5 |
| | Three-lined catfish | *Corydoras trilineatus* | Costia | 4 |
| Lori-cariidae | Spoiled Cat-fish | *Hypostomus punctatus* | Ich | 8 |
| Schil-beidae | Glass Catfish | *Ktyptopterus bicirrhus* | Ich, Fungus | 12 |
| Osteo-glossidae | Arowana | *Osteoglossum bicirrhosum* | Ich | 3 |

Brackish Water and Marine Fishes

| FAMILY | COMMON NAME | SPECIES NAME | INFECTION | NUM-BER TREAT-ED |
|---|---|---|---|---|
| Toxotidae | Archer Fish | *Toxotes jaculator* | Fungus | 5 |
| Scatopbagi-dae | Scat | *Scatophagus argus* | Fungus, Bacteria | 21 |
| Micro-desmidae | Firefish | *Nemateleo-*tris sp. | Amyloodin-ium | 6 |
| Zanclidae | Mooish Idol | *Zanclus cornutus* | Fungus | 2 |
| Cirrhitidae | Hawkfish | *Cirrhites oxycephalus* | Fungus | 5 |
| Grammati-dae | Royal Gramma | *Gramma loreto* | Amylo-odinium | 7 |
| Pseudo-chromidae | Dottyback | *Pseudochromis* spp | Dino-flagellates | 22 |
| Plesiopidae | Comet | *Calloplesiops altivelis* | Dino-flagellates | 4 |
| Apogonidae | Cardinal Fish | *Apogon fasciatus* | Bacteria, Fungus | 24 |
| Chaetodon-tidae | Butterfly Fish | *Chaetodon auriga* | Dino-flagellates, Bacteria | 36 |
| | | *Heniochus sp.* | Dino-flagellates | 5 |
| Poma-catithidae | Emperor Angel Fish | *Pomacanthus imperator* | Dino-flagellates, Fungus | 8 |
| | French Angelfish | *Pomacanthus paru* | Dino-flagellates | 1 |
| | | *Centropyge* | Bacteria, Fungus | 11 |
| | Rock Beauty | *Holacanthus tricolor* | Dino-flagellates | 3 |
| Serranidae | Anthias | *Luzonichthys* sp. | Dino-flagellates | 4 |
| Labridae | Rainbow Wrasse | *Thalassoma amblycephalus* | Fungus | 8 |
| Acanthuridae | Blue Tang | *Acanthurus* sp. | Dino-flagellates | 5 |
| | Yellow Tang | *Zebrasoma flavescens* | Dino-flagellates | 8 |
| | Unicorn fish | *Naso* sp. | Dino-flagellates | 2 |

-continued

Brackish Water and Marine Fishes

| FAMILY | COMMON NAME | SPECIES NAME | INFECTION | NUMBER TREATED |
|---|---|---|---|---|
| Pomacentridae | Damsel Fish | *Dascyllus aruanus* | Dinoflagellates, Fungus, (1) | 28 |
| | Chromis | *Chromis* sp. | Dinoflagellates | 12 |
| | Blue Damselfish | *Pomacentrus coeestis* | Dinoflagellates | 3 |
| | Anemone Fish | *Amphiprion* sp | Dinoflagellates | 6 |
| Blenniidae | Neon goby | *Elacatinus oceanops* | Dinoflagellates, Fungus | 22 |
| Gobiidae | Catalina Goby | *Lythrypnus dalli* | Bacteria, Dinoflagellates | 8 |
| | Sleeper Goby | *Valenciennea* sp | Fungus | 3 |
| | Bumblebee Goby | *Brachygobius zanthozonus* | Dinoflagellates | 9 |
| | Rainford's Goby | *Amblygobiuis rainfordi* | Fungus | 1 |
| Holocentridac | Squirrel Fish | *Myripristis* sp. | Dinoflagellates | 8 |
| Scorpaenidae | Lion Fish | *Pterois volitans* | Dinoflagellates | 2 |
| | Zebra Lion Fish | *Dendrochirus zebra* | Dinoflagellates | 2 |
| Plotosidae | eel Catfish | *Plotosus* sp. | Dinoflagellates | 4 |
| Syngnathidae | Sea Horse | *Hippocampus kuda* | Exophiala sp., (4) | 7 |
| Tetraodontidae | Puffer Fish | *Tetraodon* sp. | Amyloodinium | 6 |
| Balistidae | Black Niger | *Odonus niger* | Dinoflagellates | 2 |
| | Trigger Fish | *Balistes* sp. | Dinoflageliates | 4 |

Amphibians and Reptiles

| FAMILY | COMMON NAME | SPECIES NAME | INFECTION | NUMBER TREATED |
|---|---|---|---|---|
| Hylidae | Green Tree Frog | *Hyla cinerea* | | 8 |
| | Red-eyed Tree Frog | *Agalychnis callidryas* | | 4 |
| Ranidae | Bullfrog | *Rana catesbeiana* | | 3 |
| Xenopidae | African Clawed Frog | *Xenopis laevis* | | 9 |
| Dendrobatidae | Poison Frog | *Dendrobaies* spp. | | 12 |
| Scaphiopodidae | Spadefoot Toad | *Scaphiopus holbrookei* | | 4 |
| Proteidae | Mudpuppy | *Necturus maculosus* | | 7 |
| Salamandridae | California Newt | *Taricha torosa* | | 4 |
| Ambystomidae | Spotted Salamander | *Ambystoma maculata* | | 14 |
| Emydidae | Eastern Box Turtle | *Terrapene carolina* | Bacteria | 4 |
| | Red Eared Slider | *Pseudemys scripta* | Bacteria | 51 |
| | Pacific Pond Turtle | *Clemmys marmorata* | Bacteria | 15 |
| | Western Painted Turtle | *Chrysemys picta* | Bacteria | 5 |

Following are specific examples of tests performed on infected and healthy fishes, amphibians and turtles to further explain the nature of the results of this invention.

TEST EXAMPLE 1

A freshwater aquarium with 16 Glass Fish (*Ambassis lala*) that had been imported from Malaysia the previous week had become heavily infested with thousands of white cysts of "Ich", *Ichthyophthirius multifilis*, over the surface of their heads and bodies. Each cyst is reported in the technical literature to contain approximately 1000 young. Usually an infection of Glass Fish to this extent results in certain death to most or all. It is very rare when an "Ich" infection subsides without intensive treatment with an effective chemical remedy. The "Ich" cysts were gone and there was no indication of reinfection after 5 days, indicating the death of their young precluding reinfection. The Glass Fish were closely monitored for another three weeks without reinfection. Since the water was maintained at 75 degrees Fahrenheit (=25 degrees Centigrade) the life cycle for the "Ich" would be 3–4 days for young to hatch from the cysts, within which time a new infection of white cyst spots would be seen from the young reattaching to the fish and reproducing. No reinfection was found or reported by the subsequent keeper of these fishes in the next months. No treatment was used other than the "*Juglans* blend". "Ich" is a major problem in infecting fishes both in freshwater (protozoans), and saltwater (dinoflagellates). A successful treatment is of significance for aquarium and ornamental pond keeping, aquiculture (fish farming), handling of bait fish for sport fishing, transportation and air shipping of fishes, and government agencies involved with raising fishes for maintaining and recovering fisheries and sport fishing.

It was also found in this and all subsequent tests on the "*Juglans* blend" that there were no ill effects to the human handlers, including children handlers, of the "*Juglans* blend". As tests continued, there was accidental misuse" of the "*Juglans* blend" where by it was swallowed by pets (dogs and cats) and young children. In all cases no ill effects resulted. Therefore, the "*Juglans* blend" has considerable advantages in safety as well as in efficiency of use for man and his pet animals.

TEST EXAMPLE 2

A freshwater aquarium with 17 Scats (*Scatophagus argus*) that had been recently imported from Singapore arrived with deep open body wounds infected with bacteria *Aeromonas* sp., and with growths of white fungus *Saprolegnia* sp. on the posterior part of their body and dorsal, anal, and caudal fins. Three died before treatment was started about 8 days after being received by air shipment. The wounds, which were likely started from the fish attacking each other under crowded conditions and then becoming infected with bacteria (*Aeromonas*), started to heal after four days and required three weeks for the wounds to close and the scales to start to form. The fungus *Saprolegnia* sp. disappeared over six days and did not reappear. The fish were observed for four months and did not have a recurrence of either a bacterial or fungal infection and remained in good health. Water was maintained at 72 degrees F. (22 degrees C.). No treatment was used other than the "*Juglans* blend".

The significance of this test was in being one example of many showing that the "*Juglans* blend" treatment was effective in controlling two other external groups of external infections in fishes (bacteria and fungus). As in the case of the protozoan "Ich" a successful treatment is of significance for aquarium and ornamental pond keeping, aquiculture (fish farming), handling of bait fish for sport fishing, shipping of fishes, and for government agencies involved with raising fishes.

TEST EXAMPLE 3

A community marine aquarium with a mix of 20 fishes–6 Damsel Fishes, 4 Gobies, 2 Yellow Tangs, 3 Butterfly Fishes, 4 Angel Fishes, and a Canthigaster Puffer Fish became infected with "Marine Ich" *Amyloodinium dinoflagellates*, apparently introduced when a new import from Indonesia (the Puffer Fish) was placed in the aquarium. Five fish (2 Angels and 3 Butterflies) were also infected with Fungus. Two Damsel Fishes died before treatment. The Amyloodinium infection disappeared from the fishes completely within 14 days. Under normal circumstances without treatment more fishes would have died from the Amyloodinium infection, which once started is extremely persistent. The aquarium, fish were monitored for 6 months. The fish did not have a recurrence of the *Amyloodinium* or Fungus or any other apparent infection, and were in good health. Water was maintained at 78 degrees F. (26 degrees C.) during the test and 72 degrees F. (22 degrees C.) thereafter. No treatment was used other than the "*Juglans* blend".

The significance of this and other tests on marine and brackish-water fishes was to demonstrate that the "*Juglans* blend" was as effective in treating fishes in saltwater conditions as it was in fresh water at the same dosage levels for both. This and other tests showed that healthy fishes were essentially unaffected by the "*Juglans* blend", and that its therapeutic affect was on infectious organisms within the bacteria, single-celled plant forms (dinoflagellates) single-celled animals (protozoans), as well as multicellular infectious fungi. Also, in this and other tests it was found that the growth of single-celled algae (Chlorophyceae) was significantly suppressed from the aquaria. (See results and significance of this in Test Examples 4 and 5).

TEST EXAMPLE 4

A group of eight freshwater aquariums interconnected by a filtration system in a commercial facility were treated due to 53 Platy Fishes (*Xiphophorus maculatus*) being heavily infected with "Ich" that had been placed in one of the aquariums. This infection can be spread by the tomites (young stage) of the "Ich" protozoan by being transported through the interconnected water system to all the other aquariums. The aquatic animals in the other 7 aquariums were of 12 families and 38 species of fishes and 1 species of amphibian (spotted salamander *Ambystoma maculata*), none of which showed signs of diseases or wounds. None of the fishes in the other aquariums showed stress or became infected with "Ich" or other external diseases. The amphibians did not become infected or show signs of stress during the treatments. The "Ich" infection in the platy fishes in the one aquarium disappeared completely within 10 days. The 8 aquariums and fishes were monitored for 6 months and did not have a recurrence of the "Ich" or any other apparent external infection, and were in good health. Water was maintained at 72 degrees F. (22 degrees C.). No treatment was used other than the "*Juglans* blend".

This test and Test Example 5 below showed that a wide variety of freshwater fishes could be effectively treated with the "*Juglans* blend", and that this treatment could also be used as a preventative against a range of disease organisms in the water and externally on the aquatic animals, including pathogenic bacteria, protozoans, dinoflagellates and fungus. The tests also showed that the "*Juglans* blend" not only was effective in treating infected fishes, but could be used in the same aquarium system as healthy fishes without adverse results. Chemical treatments currently used, for examples, malachite green and formalin are to some extent detrimental to fragile aquatic animals, such as characid tetras, mormyrid elephant-nosed fishes, gymnotid electric eels, and freshwater dasyatid electric rays. The "*Juglans* blend" was effective on the fragile species of infected fishes without increasing mortalities as would otherwise be the case. Also, the tests showed that the flowering aquatic plants that were also in the aquarium systems were not affected by the "*Juglans* blend", and therefore could be used in decorative aquaria without regard to treating the fishes and other aquatic animals with the "*Juglans* Blend".

It was also observed that the "*Juglans* blend" acted as an effective suppressant (growth and reproduction) and eliminator of single-celled algae (species of Chorella and related Chlorophyceae) in the aquariums. Since such algae is normally considered a detriment in aquarium (and ornamental pond) keeping, this attribute is a definite advantage and important claim for the use of the "*Juglans* blend" in aquariums and ponds.

TEST EXAMPLE 5

In a commercial facility a group of ten freshwater aquariums interconnected by a filtration system (Group 1) were treated for external diseases with the "*Juglans* blend". Four duplicate groups of aquarium systems, each having 8–10 freshwater aquariums interconnected by a filtration system (Groups 2–5) were used as controls and received no treatment. Each system had 135–140 gallons of water circulating through all the connected aquariums. Each aquarium system of 8–10 aquariums variously had a total of 212 to 315 fishes, of 6–10 families and of 13–45 species of fishes, and 0–2 species of frogs, and 1 species of salamander. The treated system of ten aquariums had 225 fishes and 8 families and 20 species of fishes, two species of amphibians: frogs (18 individuals), and 1 species of salamander (8 individuals). All of these animals had been recently received in air shipments from exporters in the Philippines, Singapore, Indonesia, Brazil, and fish farms in Florida. When the test started it appeared that none of the animals, both in the treated system and the control systems had exterior signs of infection, although as is usual under these circumstances the stress of shipment will often result in infected animals within three weeks of arrival. Aquatic animals were introduced to and removed from the systems throughout the tests as animals were received in shipments and sold to buyers.

The Treated system received daily treatments of "*Juglans* blend" for a period of 4 weeks. The control systems received no treatment during the 4 weeks of the test. In the treated system none of the vertebrate animals (fishes, frogs, salamanders) became infected with external diseases. 18% of the fishes in the controls became infected and were removed during the test period to separate aquariums for treatment. The "*Juglans* blend" was lethal to Ramshorn snails (*Planorbis corneus*) in two of the four aquariums in which they were present, and lethal to the metazoan parasitic fish lice (*Ergasilis* sp., *Argulus* sp.) and anchor worms (*Lernaea* sp.) in one out of the three aquariums in which they were variously present. (In other tests in which the "*Juglans* blend" was at substantially greater doses, there was increased lethality for these organisms). No reproduction or growth was observed in the snails and parasites during the test period. This and other tests established that the "*Juglans* blend" at least suppressed growth and reproduction in them. Water was maintained at 72 degrees F. (22 degrees C.). No treatment was used for the treated system other than the "*Juglans* blend".

It was estimated by the handlers at the commercial facility where the test was completed that without the use of the "*Juglans* blend" there would normally have been about 15–20% of the fishes in Group 1 that would have developed infections from external diseases (bacteria, fungus, protozoans, dinoflagellates). Subsequently, the tests were repeated over ten times in varying conditions on groups of freshwater and saltwater aquariums interconnected by filtration systems. The "*Juglans* blend" continued to act as a suppressant to external infections for the healthy fishes, and to eliminate external infections of bacteria, fungus, protozoans, and dinoflagellates in infected fishes. It was also observed that the "*Juglans* blend" acted as a suppressant (growth and reproduction) and eliminator of single-celled algae (Chlorella spp., of Chlorophyceae) in the test aquariums, which is advantageous to aquarists and pond keepers wanting to keep the water clear.

In many of the freshwater aquariums where tests were done on infected fishes with the "*Juglans* blend" in the Commercial Facilities, there were various aquatic amphibian species present, and in some of the aquariums aquatic turtle species (reptiles). The "*Juglans* blend" had no adverse affect on the reptiles and amphibians in any of the tests. (See reference to amphibians in test 5). Many amphibians have toxic skin and therefore are resistant to diseases that affect fishes. Therefore, there were no examples of infected aquatic amphibians during the test period on which to try the "*Juglans* blend". However, there was the ability to test the "Juglans blend" on reptiles, for example, on two aquariums with Red-Eared Slider Turtles (*Pseudemys scripta*) in which they were seriously infected with *Salmonella* bacteria in the "leg-pit" region where their legs join their bodies. There were 12 infected in one aquarium and 9 in the other. The two aquariums received daily treatments of "*Juglans* blend" for a period of 2 weeks. By the end of this period scrapings from the "leg pits" of the turtles showed no bacteria present when examined under a compound microscope. Subsequently, such treatments have been done on this and other species of aquatic turtles with similar results.

The significance of these tests is that millions of aquatic turtles are sold annually in pet shops to hobbyists and pet keepers. The turtles are susceptible to being infected with *Salmonella* bacteria in their "leg pits" and between their body and their shells, such as at the base of their necks. Young children can be seriously infected from handling such turtles. There are cases of children dying from salmonella poisoning from putting small turtles in their mouths. A simple treatment with the "*Juglans* blend" that otherwise is harmless to the turtles, children and adults is an important innovation.

What is claimed is:

1. A method of treating a living injured or diseased aquatic animal which comprises adding to the water containing said animal, an aqueous mixture of walnut husks or a combination of walnut husks and walnut leaves in an amount effective to promote recovery of said animal.

2. The method as set forth in claim 1 in which the aqueous solution by volume contains about 3.75% to about 8.84% of said walnut husks or a combination of walnut husks and walnut leaves.

3. The method as set forth in claim 2 in which about one sixth fluid ounces of said aqueous solution mixture is added to about 5 to 10 gallons of water containing the said animal on a daily basis.

4. The method as set forth in claim 3 in which said mixture is added twice a day.

* * * * *